United States Patent [19]

Ibrahim et al.

[11] Patent Number: 4,541,431
[45] Date of Patent: Sep. 17, 1985

[54] USE OF TELEMETRY COIL TO REPLACE MAGNETICALLY ACTIVATED REED SWITCH IN IMPLANTABLE DEVICES

[75] Inventors: Ibrahim H. Ibrahim, North Ryde; Christopher N. Daly, Bilgola Plateau, both of Australia

[73] Assignee: Telectronics Pty. Ltd., Lane Cove, Australia

[21] Appl. No.: 652,290

[22] Filed: Sep. 20, 1984

[51] Int. Cl.$^4$ .............................................. A61N 1/36
[52] U.S. Cl. ............................... 128/419 PT; 128/903
[58] Field of Search .................. 128/419 PG, 419 PS, 128/419 PT, 903

[56] References Cited

U.S. PATENT DOCUMENTS

| | | | |
|---|---|---|---|
| 4,223,679 | 9/1980 | Schulman et al. | 128/419 PT |
| 4,361,153 | 11/1982 | Slocum et al. | 128/419 PT |
| 4,453,162 | 6/1984 | Money et al. | 128/903 |
| 4,494,545 | 1/1985 | Slocum et al. | 128/903 |

Primary Examiner—William E. Kamm
Attorney, Agent, or Firm—Gottlieb, Rackman & Reisman

[57] ABSTRACT

A combined telemetry system and magnetic field sensor for use in an implantable medical device. The telemetry system includes a conventional resonant circuit for transmitting and receiving data. The resonant circuit has a coil which is also used to sense the presence of a magnetic field exceeding a threshold value. The resonant frequency varies with the strength of the magnetic field which passes through the coil. Periodically, the resonant circuit is energized, and during a sensing window of predetermined duration which then immediately follows the voltage across the coil is examined for a predetermined number of zero crossings. That number of zero crossings will occur only in the presence of a magnetic field whose amplitude exceeds the threshold value. It is possible to achieve a sensitivity in such a system which is comparable to that of conventional miniature reed switches.

14 Claims, 3 Drawing Figures

USE OF TELEMETRY COIL TO REPLACE MAGNETICALLY ACTIVATED REED SWITCH IN IMPLANTABLE DEVICES

DESCRIPTION

This invention relates to implantable medical devices, and more particularly to the use of the standard telemetry coil found in devices such as a pacemaker not only for its usual purpose, but also as a replacement for the conventional magnetically activated reed switch.

For many years, reed switches have provided a mechanism for the non-invasive activation of functions within an implantable medical device, such as a pacemaker. For example, permanent magnets have been used to close a reed switch in order to disable the demand function of a pacemaker; this has often been done to cause the pacemaker to pace at a rate which is related to battery condition. Permanent magnets have also been used in the same fashion to enable a special temporary pacing mode, such as one suitable for tachycardia reversion. Another very common use of reed switches is to enable the reception of magnetic-pulse and coded data for programming pulse generator parameters.

High-reliability, miniature, hermetically-sealed reed switches have been developed specifically to meet the requirements of the pacemaker industry. The use of a magnet to cause the pacer to pace at a rate dependent on battery condition has become standard practice. But with the rapid increase in sophistication of implantable pulse generators, it has become essential to provide greater two-way communication with the pulse generator, this communication broadly embracing programming, interrogation, telemetry, and the furnishing of electrophysiological data. The means for two-way communication is typically via low-frequency R.F. energy, using a coil inside the pulse generator for both transmission and reception.

In our co-pending application filed on even date herewith, entitled "Electronic Sensor For Static Magnetic Field," we disclose how a magnetic field can be sensed using a coil sensor whose operating DC current is relatively low, whose size is small, and whose sensitivity to a static magnetic field is high, while at the same time having a low sensitivity to noise, interference, and supply voltage fluctuations. The coil has a ferromagnetic core and it functions to sense an external magnetic field due to the decrease in inductance as the external field forces the core further away from the origin of the B-H curve. It is an object of the present invention to provide not a stand-alone sensor as disclosed in our copending application, but rather a combined sensor/telemetry coil, in the context of an overall system which allows the same coil to be used both for two-way communication and for sensing the presence of an external magnetic field. With use of our invention, it is possible to retain the "magnetic test" function of a standard pulse generator, while no longer requiring use of a fragile and relatively costly component, the standard reed switch.

In accordance with the principles of our invention, the magnetic-field detection circuit uses much of the existing circuitry to be found in a standard telemetry transceiver system. Control logic is added in order to provide the appropriate coil excitation as well as decision logic which disables the magnetic-field detection function while telemetry is in progress. We have found that using the approach of our invention, it is possible to achieve a detection range which is comparable to that of a reed switch under the same conditions. The energy consumed by the test circuit can be made almost negligible by triggering the magnetic-field test sequence at a rate of once or twice per second. At a rate of once per second, the average current required for the test is only 10 nanoamperes.

Further objects, features and advantages of our invention will become apparent upon consideration of the following detailed description in conjunction with the drawings, in which.

As disclosed in our co-pending application, which is hereby incorporated by reference, the magnetic-field test sequence entails the generation of two signals, "excitation" and "sensing," the latter following the former and each having a predetermined duration. The excitation signal excites a coil. The coil is included in a resonant circuit, and a resonant current then flows. The sensing signal defines a window, and the resonant current exhibits different zero crossing characteristics during the sensing window in the presence and absence of a magnetic field of sufficient intensity. In the illustrative embodiment illustrated in our co-pending application, a strong enough magnetic field reduces the dynamic permeability of the coil, giving rise to a higher ringing frequency so that a zero crossing point of interest is shifted inside the sensing window. A similar principle of operation is employed in the subject invention.

Figure 1:
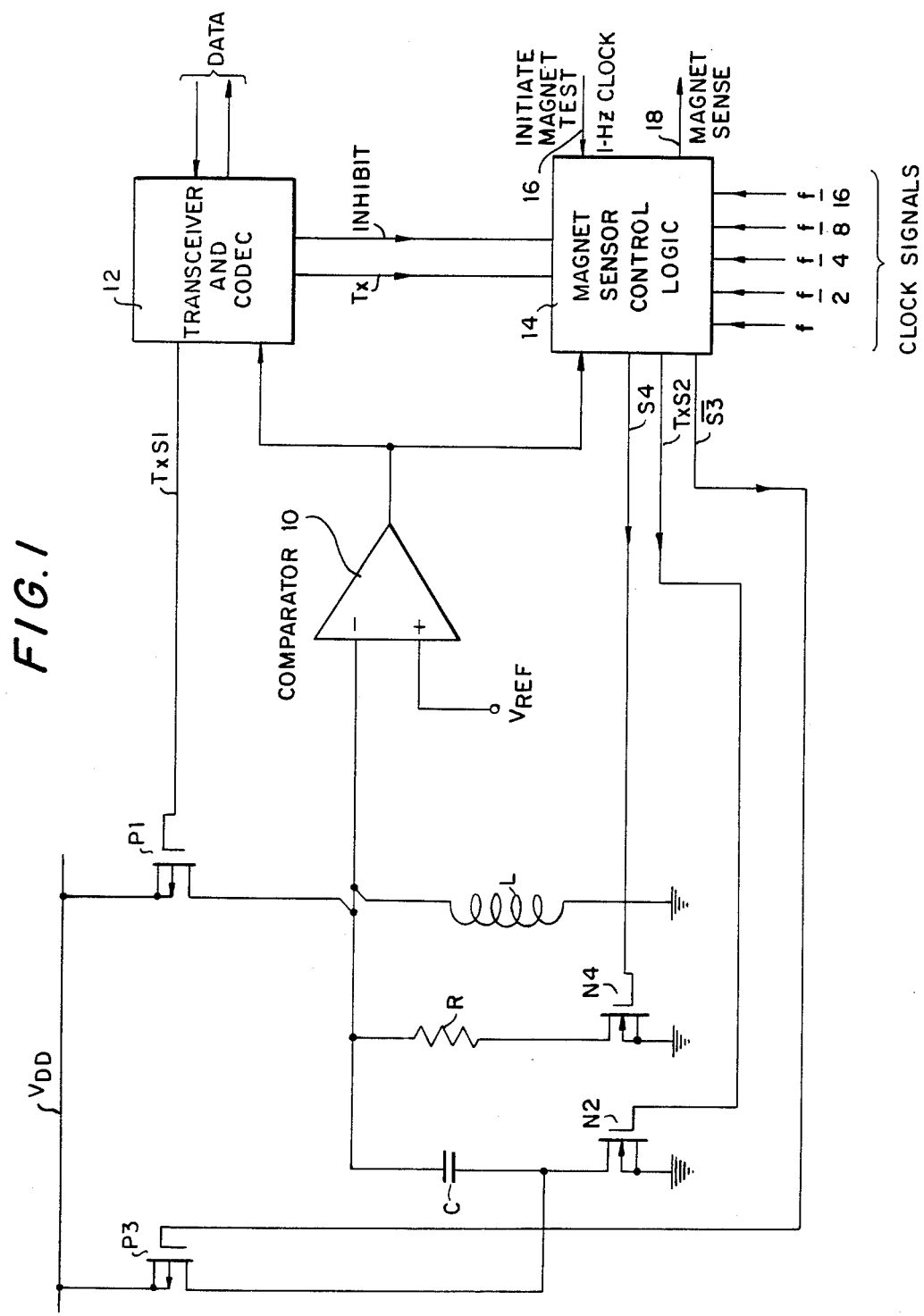
FIG. 1 is a block diagram of a typical telemetry transceiver front end, as used in an implantable pacemaker, with the illustrative magnetic-field test circuit of our invention added.

When the system of FIG. 1 is in the transmit mode, magnet sensing is inhibited. In this case switch N2 is closed to connect capacitor C and inductor L in parallel. As is conventional practice, transmitted bursts are controlled when transceiver and codec 12 closes switch P1, thus connecting the power source $V_{DD}$ across the resonant circuit. The transceiver and codec 12 determines the period of the transmission and the data rate, in accordance with a data input. A burst is controlled when conductor TxS1 is pulsed low.

When the system is operating in the receive mode, both of switches P1 and N2 are open-circuited, allowing the coil L to pick up the R.F. data. The voltage induced across the coil causes the output of comparator 10 to pulse and a data signal is thus transmitted to the transceiver and codec 12. The system of FIG. 1 operates in a conventional manner when transmitting and receiving data.

The additional function of sensing a static magnetic field is initiated for a very short period of time when the system is in its receive mode. This reduces the chance of a magnet signal overriding received data. In the illustrative embodiment of the invention, the magnet-sensing function is initiated once a second in order to minimize the average current consumption.

Figure 3:
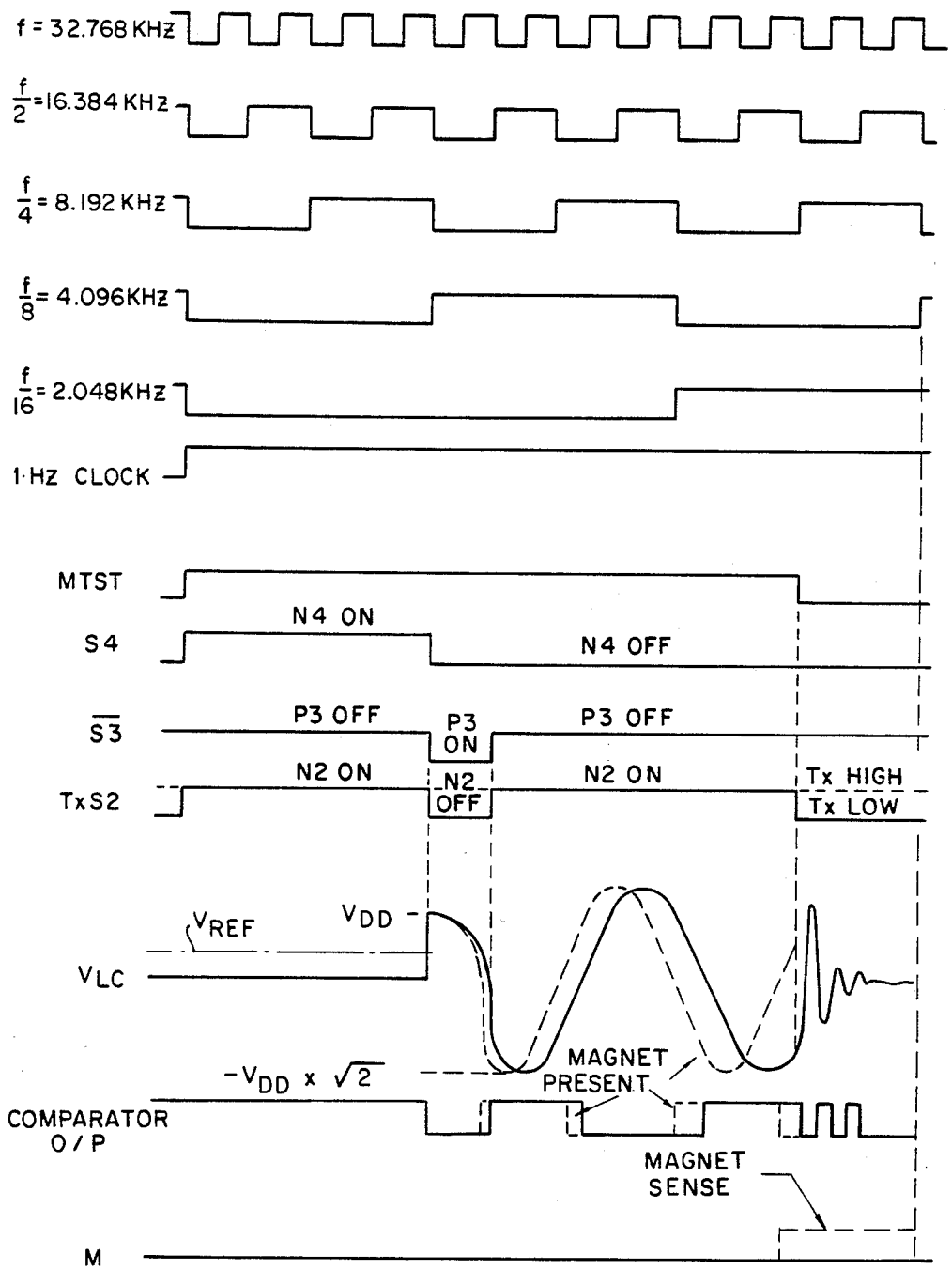
FIG. 3 depicts the digital signals, and the excitation and response waveforms, which characterize the circuits of FIGS. 1 and 2.

In the illustrative embodiment of the invention the values of L and C in the tuned circuit are chosen so that they have a resonant frequency of 8 KHz, slightly less than 8.192 KHz (a binary multiple of 1 Hz). Referring to FIG. 3, at the start of the cycle both of signals S4 and TxS2 go high so that switches N2 and N4 close. Referring to the clock waveforms at the top of FIG. 3, the two switches are closed for 122 microseconds in order to discharge capacitor C through resistor R. The resistor is used to limit the current and to protect the switches. After the capacitor is discharged, the S3 signal goes low as indicated in FIG. 3 for a period of 30.5 microseconds, while the S4 and TxS2 signals also go low. At the same time that switches N2 and N4 are now off, switch P3 is closed. At the end of the 30.5-microsecond excitation interval, switch P3 opens while switch N2 closes for 151.5 microseconds. (Switch N4 remains off during this interval.) The voltage across the resonant circuit, shown as $V_{LC}$ in FIG. 3, has two parts—excitation and response. The excitation part of the signal is controlled by the conduction of switch P3 when excitation interval of 30.5 microseconds. The response ensues during the 151.5-microsecond interval when the switch N2 is the only switch which is closed, allowing the capacitor and the inductor to resonate, and the output of comparator 10 to change state as the voltage at the minus input of the comparator passes the $V_{REF}$ reference level.

Figure 2:
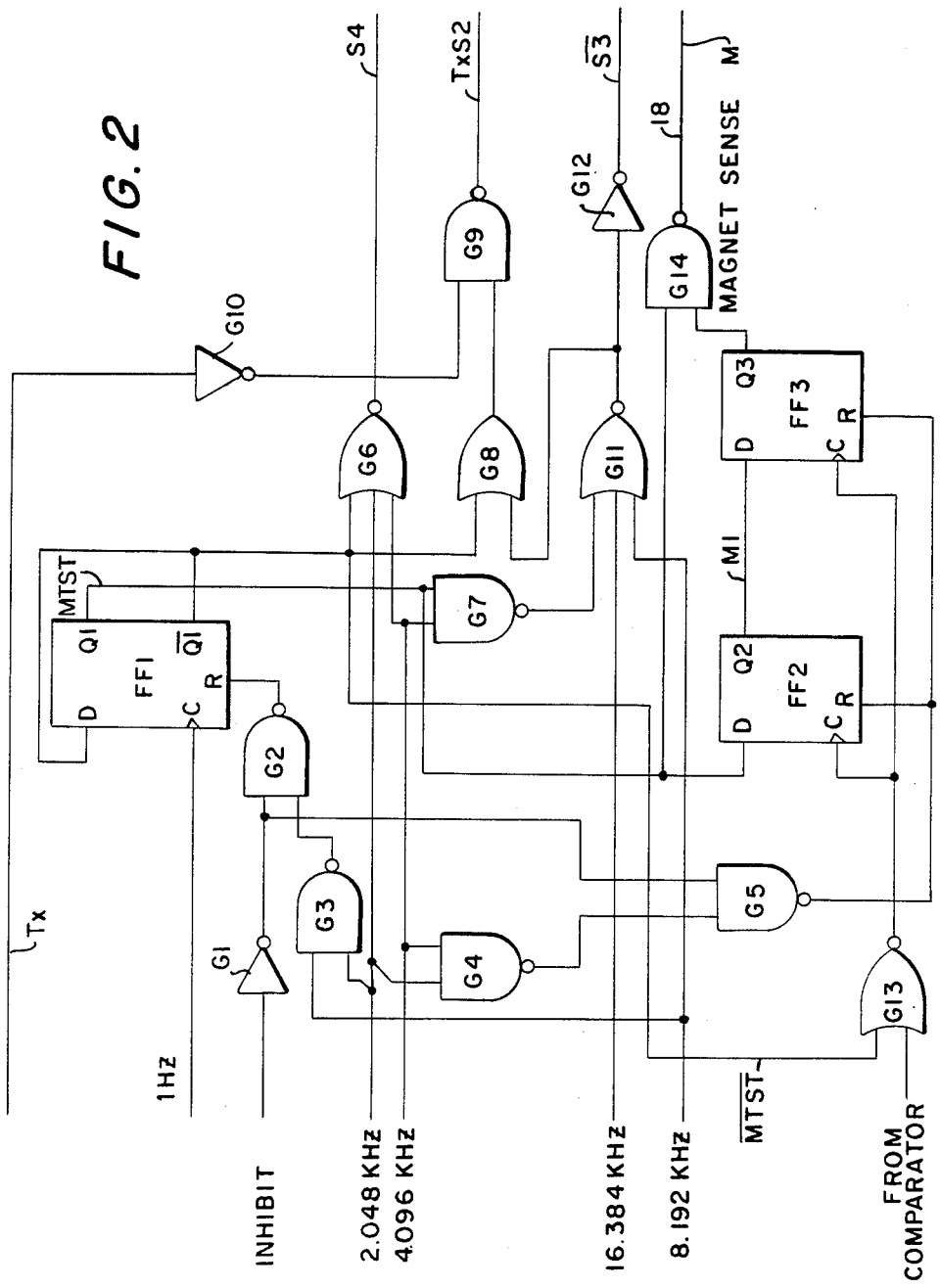
FIG. 2 depicts logic circuits for controlling operation of the system of FIG. 1.

The logic used to generate the required switching signals is shown in block 14 in FIG. 1, and the detailed circuitry of this block is shown in FIG. 2. There are five clock signals which are connected to inputs of the magnet sensor control logic 14, and the five clock signals are shown at the top of FIG. 3. Another input is applied to conductor 16, a 1-Hz clock signal which initiates a magnet test when the input goes high. The inhibit input prevents initiation of the magnetic field sensing, the inhibit input being pulsed by the transceiver and codec 12 when the coil is required for another function. Other inputs to block 14 are the output of comparator 10 and the Tx signal from transceiver and codec 12. The three output signals from block 14, as shown in FIG. 3, are S4, TxS2 and S3.

When the 1-Hz clock signal goes high, flip-flop FF1 is triggered. Since its Q1 output is normally high, and because it is connected to the D input, the flip-flop is set and the Q1 output (MTST) goes high. The MTST signal is the master signal for triggering the magnet test. If the inhibit signal is high, however, the output of gate G1 is low, and therefore the output of gate G2 is high to hold flip-flop FF1 reset. Assuming that a test sequence does occur, the flip-flop is reset, as shown in the drawing, when both of the 2.048-KHz and 8.192-KHz signals are first high. At this time the output of gate G3 goes low and the output of gate G2 goes high to reset the flip-flop. With the clocks having the rates shown in FIG. 3, the output of gate G3 goes low 305 microseconds after the MTST signal first goes high. The total time required for performing the overall test is 366 microseconds, as will be discussed.

It should be noted that the magnet sensor control logic is driven from a plurality of clock signals, the highest of which is 32.768 KHz. The subharmonic clock signals are derived from this highest frequency, which itself is normally available from a 32.768-KHz crystal oscillator used as part of the telemetry system.

Switch P1 in FIG. 1 is closed only when the system operates in the transmit mode, and is controlled by transceiver and codec 12. Signals controlling switches N2, N4 and P3 are generated in block 14. Switch N2 is controlled by logic signal TxS2 which goes high to turn switch N2 on. Referring to FIG. 2, it is gate G9 which causes signal TxS2 to go high. When the system is transmitting data, the Tx control signal from transceiver and codec 12 is high. Thus the output of gate G10 on FIG. 2 is low and the output of gate G9 is high. With the TxS2 conductor high in potential, switch N2 is held on so that capacitor C and inductor L are connected in parallel as required for transmission. In the receive mode, the Tx signal is low and the output of gate G10 is high. Thus the state of signal TxS2 depends on the operation of gate G8 exclusively. When the magnet test is not being performed, since the Q1 output of flip-flop FF1 is high, the output of gate G8 is also high, and thus the output of gate G9 is low to hold switch N2 off. But during the magnet test the Q1 output of the flip-flop is low and thus the operation of gate G8 is controlled exclusively by gate G11. It is at this time that the other gates control the TxS2 signal.

Gate G11 is controlled by two clock signals and gate G7, the latter gate being controlled by still a third clock signal (as well as the MTST enabling signal). Following the logic, gate G11 has its output normally low, with the output going high only for the short interval when S3 on FIG. 3 is shown low. It is gate G11 which in fact derives the S3 signal through gate G12. The output of gate G8 is the same as the output of gate G11 whenever the MTST signal is high. The S4 signal is derived by gate G6 from two clock signals during the time that flip-flop FF1 remains set.

Referring to FIG. 1, $V_{LC}$ (the input at the minus input of comparator 10) is normally smaller in magnitude than the reference potential, and the comparator output is normally high. This is shown in FIG. 3. How the comparator output changes during the test cycle will be described below, as will the manner in which this affects flip-flops FF2 and FF3, and output gate G14. It should be noted at this point, however, that whenever the inhibit signal goes high, the output of gate G1 goes low, and the output of gate G5 goes high to reset both flip-flops, in effect disabling the magnet test output. Similarly, at the end of a normal test sequence, when the MTST signal goes low, the Q1 output of flip-flop FF1 ($\overline{MTST}$) goes high and the output of gate G13 goes low. This prevents flip-flops FF2 and FF3 from being clocked, i.e., they remain reset. Even if they were previously set during a test cycle, they are reset when the output of gate G4 goes low to cause the output of gate G5 to go high, and they then remain reset. The output of gate G4 goes low when its two clock inputs are first high. This occurs after one and a half cycles of the 2.048-KHz clock, as shown in FIG. 3 (at the right end of the drawing). It should be noted that if the MTST signal is high and flip-flop FF3 is set, then the output of gate G14, the magnet sense (M) conductor 18, has its state controlled by the state of flip-flop FF3. The flip-flop is set during the sensing interval if the strength of the magnetic field under test exceeds a threshold level. Flip-flop FF3 should be interrogated only at the tail end of the overall test cycle, during the "magnet sense" interval shown at the bottom of FIG. 3.

A full test cycle in the illustrative embodiment of the invention requires 366 microseconds, at 1-second intervals. If an external programmer sends the data which is required to establish a telemetry communication link with the system during the MTST test period, then the communication link will not be established. This is because the programmer expects an echo from the telemetry device which acknowledges and confirms reception of a valid command to start communication. But during the magnet test, the coil will not be able to transmit any echo, much less the correct one. That will be treated by a conventional pacemaker programmer as an error condition and the programmer will re-transmit the data after a short delay. An error simply means that either the telemetry device or the programmer was confused by the presence of invalid signals. The next time that an attempt is made to establish a telemetry communication link, the magnet test will not be on and a communication channel can be established. This causes an inhibit signal to be generated by the transceiver and codec block 12, thus permanently disabling the magnet test until the communication link is broken at the end of the telemetry sequence.

At the beginning of the magnet test cycle, switches N2 and N4 close for 122 microseconds in order to remove any residual charge from capacitor C in FIG. 1. This is the "preconditioning" period. The lower side of the capacitor is then pulled up to the $V_{DD}$ potential for 30.5 microseconds when switch P3 is turned on, as shown in FIG. 3. This causes a cosinusoidal voltage waveform of amplitude $V_{DD}$ across the coil. At the end of the 30.5-microsecond period, switch P3 opens and switch N2 closes once again. This time the side of the capacitor connected to switch N2 is connected to ground, thus causing an additional negative excitation step across the capacitor. The voltage across the coil from this moment until the end of the magnet test period can be expressed as $V_{LC}=(-2^{\frac{1}{2}})(V_{DD}) \sin(w_0 t + \pi/4)$. In the absence of a magnetic field, the values of L and C result in a resonant frequency of approximately 8 KHz.

The response "ringing" waveform and the corresponding comparator output for this case are shown by the solid lines at the bottom of FIG. 3. The comparator output has a single negative-going edge inside the magnet test window. (The test or sensing window has a duration equal to the duration of the second conduction time of switch N2, as shown in FIG. 3.) Each negative-going edge at the output of the comparator causes the output of gate G13 to go high and clock flip-flops FF2 and FF3. The first clock causes the Q2 output of flip-flop FF2 to go high. As long as there is no second clock, the Q3 output of flip-flop FF3 remains low, and the magnet sense signal at the output remains high. The two-stage counter is reset every cycle, 61 microseconds after the end of the test window.

However, when a steady magnetic field is applied to the coil, the relative permeability of the magnetic core will be reduced, causing the ringing frequency to be higher as shown by the dotted ringing waveform in FIG. 3. The corresponding comparator output waveform will now have two or more negative going edges in the test window. The second negative-going edge will cause flip-flop FF3 to be set, since its D input is connected to the Q2 output of flip-flop FF2. The counter will be located in this state until it is reset at the end of the cycle. Thus if the output M is low for at least the last 61 microseconds of the overall cycle, it is an indication of the presence of a magnetic field.

Referring to the $V_{LC}$ waveform in FIG. 3, it will be noted that beginning with the sensing interval (during which switch N4 is off and switch N2 is on), there are two zero crossings (one positive, one negative); whether or not there is a third (positive, giving rise to a negative comparator output) depends on the frequency of the resonant circuit. In the presence of a magnetic field, the third zero crossing occurs in the window, and in the absence of a magnetic field the third zero crossing occurs after the MTST signal goes low at which time flip-flops FF2 and FF3 may not be clocked. It is only a zero crossing of $V_{LC}$ in the positive direction that results in the clocking of the flip-flops. Thus whether or not flip-flop FF3 is set depends upon whether the third zero crossing falls within the sensing window. Sensing sensitivity may be defined as the field strength required to shift the third zero crossing of the ringing waveform inside the test window, assuming that the reference voltage $V_{REF}$ of the comparator is small. The sensitivity depends on two sets of factors. The first comprises the magnetic properties of the coil core. The second comprises the shift in frequency to bring the zero crossing of interest to a position inside the test window.

The magnetic properties of the coil core depend on the shape of the core and its magnetic properties, i.e., the B-H curve. In order to achieve high sensitivity, the dynamic permeability of the core should change by a noticeable amount at the lowest field strength of interest. The core should have large-area pole faces but a small diameter.

As for the shift in frequency to bring the zero crossing point of interest to the required position inside the test window, that depends on the original position of the zero crossing point. That, in turn, is a function of the resonant frequency of the LC circuit. If the circuit is tuned to a frequency slightly lower but very close to 8.192 KHz, the sensitivity will be extremely high but the system may be affected by noise or interference. Excellent noise rejection and good sensitivity may be achieved when the resonant frequency is adjusted to 8 KHz. In actual practice, the sensitivity can be made comparable to that of miniature reed switches. Excellent noise rejection results for two different reasons. First, the magnet test is carried out for 366 microseconds every second; noise can be effective only if it happens to fall in that short period. Second, the high sensitivity of the resonant circuit helps to reject all noise components to which the resonant circuit is not tuned.

The addition of the magnet test control logic to an existing telemetry system will cause a slight increase in the total DC current. Using standard CMOS logic configurations, the current can be kept to less than 0.1 microamperes. As for the current required to drive the resonant circuit, with a coil having Q=20 and with $V_{DD}=2.8$ volts, the peak current through the coil was 120 microamperes and the average value was 2.3 nanoamperes. Thus the total system current is increased by well under 0.2 microamperes. It should also be noted that if the system is supplied from the a high-impedance battery having a standard by-pass capacitor of 10 microfarads, then during the LC peak current burst the operating voltage will drop slightly below its initial value. But the drop is less than 5 millivolts and will not have any deleterious effect on the overall system operation.

Although the invention has been described with reference to a particular embodiment, it is to be understood that this embodiment is merely illustrative of the application of the principles of the invention. Numerous modifications may be made therein and other arrangements may be devised without departing from the spirit and scope of the invention.

We claim:

1. A combined telemetry system and magnetic field sensor for use in an implantable medical device comprising a tuned circuit including inductor means and capacitor means, telemetry logic means for controlling the application of energizing pulses to said inductor means when operating in a transmit mode and for sensing potentials across said inductor means when operating in a receive mode, said tuned circuit having a resonant frequency which varies with the strength of an external magnetic field which passes through said inductor means, and means for periodically sensing the presence of a magnetic field passing through said coil, said sensing means including means for applying an energizing signal to said tuned circuit for a predetermined time interval, means for defining a sensing window which begins and ends at predetermined times following energization of said tuned circuit, and means for detecting the manner in which the signal level at a selected point in said tuned circuit relates to a threshold level during said sensing window.

2. A system in accordance with claim 1 wherein said telemetry logic means inhibits the operation of said sensing means during the transmitting or receiving of telemetry signals.

3. A system in accordance with claim 2 further including means at the start of each sensing cycle for preconditioning the tuned circuit prior to the energization thereof.

4. A system in accordance with claim 3 wherein said telemetry logic means when operating in the receive mode and said sensing means share said detecting means.

5. A system in accordance with claim 4 wherein said tuned circuit rings following cessation of the energization thereof, said detecting means operates on a voltage which appears across said inductor means, and said sensing window has a duration such that a predetermined number of zero crossings occur during said sensing window only in the presence of a magnetic field having a predetermined minimum strength.

6. A system in accordance with claim 5 wherein said energizing signal is applied to said tuned circuit repetitively at periodic intervals, and said sensing window defining means and said detecting means operate at the same periodic intervals.

7. A system in accordance with claim 1 further including means at the start of each sensing cycle for preconditioning the tuned circuit prior to the energization thereof.

8. A system in accordance with claim 1 wherein said telemetry logic means when operating in the receive mode and said sensing means share said detecting means.

9. A system in accordance with claim 1 wherein said tuned circuit rings following cessation of the energization thereof, said detecting means operates on a voltage which appears across said inductor means, and said sensing window has a duration such that a predetermined number of zero crossings occur during said sensing window only in the presence of a magnetic field having a predetermined minimum strength.

10. A system in accordance with claim 9 wherein said energizing signal is applied to said tuned circuit repetitively at periodic intervals, and said sensing window defining means and said detecting means operate at the same periodic intervals.

11. A system in accordance with claim 1 wherein said energizing signal is applied to said tuned circuit repetitively at periodic intervals, and said sensing window defining means and said detecting means operate at the same periodic intervals.

12. A combined telemetry system and magnetic field sensor comprising a tuned circuit including inductor means and capacitor means, telemetry logic means for controlling the application of energizing pulses to said inductor means when operating in a transmit mode and for sensing potentials across said inductor means when operating in a receive mode, said tuned circuit having a resonant frequency which varies with the strength of an external magnetic field which passes through said inductor means, and means for periodically sensing the presence of a magnetic field passing through said coil, said sensing means including means for applying an energizing signal to said tuned circuit the response to which is a function of the strength of the external magnetic field which passes through said inductor means, and means for analyzing for the response of said tuned circuit to said energizing signal.

13. A system in accordance with claim 12 wherein said telemetry logic means inhibits the operation of said sensing means during the transmitting or receiving of telemetry signals.

14. A system in accordance with claim 12 further including means at the start of each sensing cycle for preconditioning the tuned circuit prior to the energization thereof.

* * * * *